US009802010B2

(12) United States Patent
Brown et al.

(10) Patent No.: US 9,802,010 B2
(45) Date of Patent: Oct. 31, 2017

(54) INTERPROXIMAL DRUG DELIVERY DEVICE

(71) Applicant: NOVEOME BIOTHERAPEUTICS, INC., Pittsburgh, PA (US)

(72) Inventors: Larry R Brown, Newton, MA (US); Tyler A Okel, Canonsburg, PA (US)

(73) Assignee: Noveome Biotherapeutics, Inc., Pittsburgh, PA (US)

( * ) Notice: Subject to any disclaimer, the term of this patent is extended or adjusted under 35 U.S.C. 154(b) by 186 days.

(21) Appl. No.: 14/526,644

(22) Filed: Oct. 29, 2014

(65) Prior Publication Data

US 2015/0148782 A1    May 28, 2015

Related U.S. Application Data

(60) Provisional application No. 61/907,992, filed on Nov. 22, 2013.

(51) Int. Cl.
| | | |
|---|---|---|
| *A61M 11/00* | (2006.01) | |
| *A61M 11/02* | (2006.01) | |
| *A61C 19/06* | (2006.01) | |
| *A61C 17/02* | (2006.01) | |
| *B65D 83/16* | (2006.01) | |

(52) U.S. Cl.
CPC ....... *A61M 11/007* (2014.02); *A61C 17/0202* (2013.01); *A61C 19/063* (2013.01); *A61M 11/02* (2013.01); *A61M 11/003* (2014.02); *A61M 2205/3365* (2013.01); *A61M 2205/8206* (2013.01); *A61M 2205/8243* (2013.01); *B65D 83/16* (2013.01)

(58) Field of Classification Search
CPC .............. A61M 11/007; A61M 11/006; A61M 2005/3152; A61M 2205/3317; A61M 5/3155; A61M 11/003; A61M 11/06; A61M 11/08; A61M 15/0001; A61M 15/0065; A61M 15/0066; A61M 15/009; B65D 83/16
See application file for complete search history.

(56) References Cited

U.S. PATENT DOCUMENTS

| | | | | |
|---|---|---|---|---|
| 3,976,223 | A * | 8/1976 | Jass ...................... | B65D 83/682 222/94 |
| 6,464,663 | B1 * | 10/2002 | Zinger ............. | A61B 17/00491 222/390 |
| 6,503,481 | B1 * | 1/2003 | Thurston .............. | A61K 9/0073 128/200.14 |

(Continued)

FOREIGN PATENT DOCUMENTS

EP          2060284 A1 *  5/2009

*Primary Examiner* — Bhisma Mehta
*Assistant Examiner* — Nilay Shah
(74) *Attorney, Agent, or Firm* — Law Offices of Albert Wai-Kit Chan, PLLC

(57) ABSTRACT

This present invention provides a delivery device that could be used to delivery discreet small volume of expensive biotechnology treatments to specific areas of the oral cavity, or other tissues. The present invention also provides a method of using the device disclosed herein to deliver biotechnology treatments and/or therapeutic agents to specific areas of the oral cavity, or other tissues. In one embodiment, the treatments and/or therapeutic agents are delivered to the interproximal area between and around the teeth.

15 Claims, 1 Drawing Sheet

(56) References Cited

U.S. PATENT DOCUMENTS

| | | | |
|---|---|---|---|
| 7,128,067 B2 * | 10/2006 | Byron | A61M 11/041 128/200.14 |
| 8,444,417 B2 * | 5/2013 | Golden | A61K 35/50 433/215 |
| 2003/0010336 A1 * | 1/2003 | Vito | A61M 15/0086 128/200.22 |
| 2005/0000711 A1 * | 1/2005 | Hurlstone | A61M 5/2046 173/19 |
| 2006/0129099 A1 * | 6/2006 | Kumar | A61M 3/0216 604/151 |
| 2010/0273126 A1 | 10/2010 | Janssen | |
| 2015/0017601 A1 * | 1/2015 | Fish | A61C 3/025 433/88 |

* cited by examiner

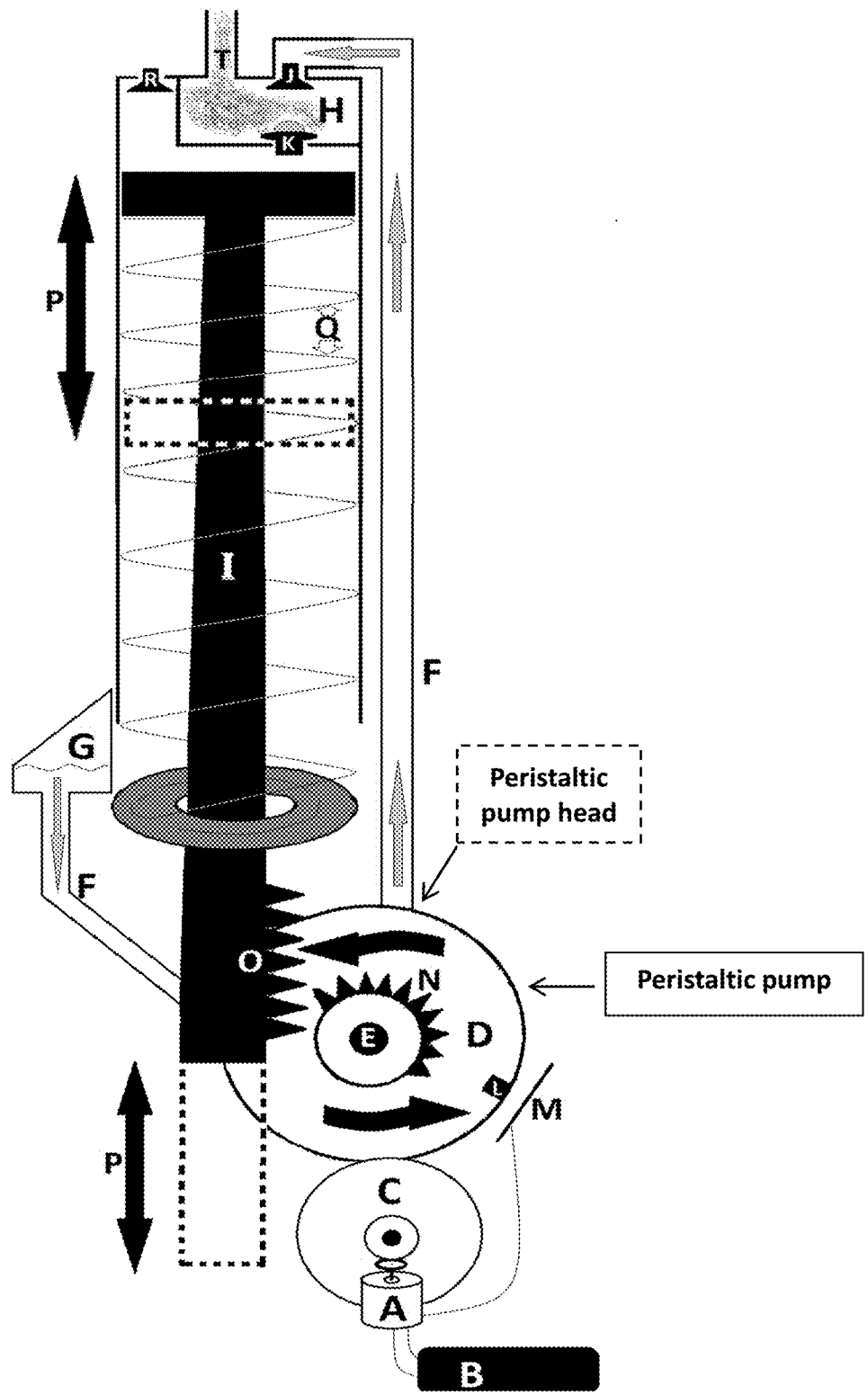

INTERPROXIMAL DRUG DELIVERY DEVICE

FIELD OF THE INVENTION

The present invention relates to a drug delivery device. In one embodiment, the present invention provides a drug delivery device useful for delivering a therapeutic agent to the interproximal area between and around the teeth.

BACKGROUND OF THE INVENTION

Gingivitis (inflammation of the gums) usually precedes periodontitis (gum disease). In the early stage of gingivitis, bacteria in plaque (a sticky, colorless film of bacteria that forms on teeth) causes the gums to become inflamed, often bleeding. At this stage the teeth are still firmly embedded in their sockets and no irreversible bone or other tissue damage has occurred. However, if left untreated, gingivitis can advance to periodontitis. In periodontitis, the inner layer of the gum and bone pull away from the teeth and form spaces called pockets. These pockets collect debris and often become infected. Toxins, which are produced by the bacteria in plaque, and enzymes produced by the body as it fights the infection, cause the breakdown of the bone and connective tissue that anchors the teeth. As the disease progresses, the pockets deepen and more bone and connective tissue are destroyed. Eventually the teeth are no longer anchored in place and become loose, often leading to tooth loss. In fact, periodontitis is the leading cause of tooth loss in adults.

Plaque is the primary cause of gingivitis and periodontitis. However, other factors can contribute to these diseases as well, including hormonal changes associated with pregnancy, puberty, menstruation, and menopause, all of which can make gums more sensitive and easier for gingivitis to develop. In addition, many illnesses can affect the gums. Such illnesses include diseases such as cancer or HIV infection, both of which can interfere with the proper functioning of the immune system. Diabetics are at generally at a higher risk of developing infections than non-diabetics, including periodontal disease. Medications can also affect oral health because some can decrease the flow of saliva, which has a protective effect on the teeth and gums. Smoking makes it harder for gum tissue to repair itself. And of course poor oral hygiene such as not brushing and flossing on a daily basis makes it easier for gingivitis to develop. A family history (genetics) of dental disease can be a contributing factor for the development of gum disease, as well.

Researchers have identified potential links between gum disease and other serious health conditions such as stroke and heart disease. Diabetes is not only a risk factor for gum disease, but gum disease may make diabetes worse.

Surgical treatments for gum disease include flap surgery/pocket reduction surgery. During this procedure the gums are lifted back and the tarter is removed. In some cases, irregular surfaces of the damaged bone are smoothed to limit areas where disease-causing bacteria can accumulate. The gums are then placed so that the tissue fits snugly around the tooth. This method reduces the size of the pockets between the gum and tooth, thereby decreasing the areas where harmful bacteria can grow. Bone grafts involve using fragments of the patient's own bone, synthetic bone, or donated bone to replace bone destroyed by gum disease. The grafts serve as a platform for the regrowth of bone, which restores stability to the teeth. New technology, called tissue engineering, encourages the body to regenerate bone and tissue at an accelerated rate. Soft tissue grafts reinforce thin gums or fills in areas where gums have receded. Grafted tissue, most often taken from the roof of the mouth, is sutured in place, adding tissue to the affected area. Guided tissue regeneration is performed when the bone supporting the teeth has been destroyed. This procedure stimulates bone and gum tissue growth. Done in combination with flap surgery, a small piece of mesh-like fabric is inserted between the bone and gum tissue. This keeps the gum tissue from growing into the area where the bone should be, allowing the bone and connective tissue to regrow to better support the teeth. Bone surgery smooths shallow craters in the bone due to moderate and advanced bone loss. Following flap surgery, the bone around the tooth is reshaped to decrease the craters. This makes it harder for bacteria to collect and grow.

Current non-surgical treatments for gum disease include professional dental cleaning to remove the plaque and tartar, which is plaque that builds up and hardens on the tooth surface, from above and below the gum line. Often a professional dental cleaning is recommended more than twice-a-year. Scaling and root planning are deep-cleaning, nonsurgical procedures done under a local anesthetic, whereby plaque and tartar from above and below the gum line are scraped away (scaling) and rough spots on the tooth root are made smooth (planing) Smoothing the rough spots removes bacteria and provides a clean surface for the gums to reattach to the teeth.

Antibiotic therapy can be used either in combination with surgery and other therapies, or alone, to reduce or temporarily eliminate the bacteria associated with gum disease or suppress the destruction of the tooth's attachment to the bone. Chlorhexidine is an antimicrobial used to control plaque and gingivitis in the mouth or in periodontal pockets. It is available as a mouth rinse or as a gelatin-filled chip that is placed in the pockets after root planing and releases the medication slowly over time. Other antibiotics, including doxycycline, tetracycline, and minocycline may also be used to treat gum disease. In addition, a nonprescription toothpaste that contains fluoride and an antibiotic to reduce plaque and gingivitis, called triclosan, may be recommended.

Many therapeutic agents in development today are complex biological substances. For example, some are cells or cell-derived substances. In contrast to small molecule agents which are relative inexpensive to make, the complex biological substances are very expensive to make. As a consequence, they are generally much higher in price than traditional small molecule agents. Therefore, there is a need to reduce the required volume of the biological substance to the lowest possible efficacious amount in order to control costs. In accordance with this goal there is a need for a drug delivery device that is capable of delivering a small volume of a therapeutic agent precisely to the interproximal area between and around the teeth. Such delivery would provide a cost-efficient treatment option for patients suffering from dental diseases, disorders or injuries, e.g., periodontal (gum) diseases.

SUMMARY OF THE INVENTION

The present invention provides a novel delivery device that could be used to precisely delivery a discreet, small volume of a therapeutic agent to specific areas of the oral cavity, gingiva or other tissues. The present invention is particularly well-suited for the precise delivery of a small volume of an expensive biological substance.

In one embodiment, the present invention provides a delivery device for delivering therapeutic agents to a subject, comprising a peristaltic pump driven by a motor, wherein the peristaltic pump comprises a peristaltic pump head and a pneumatic piston; a liquid reservoir which is connected to a mixing chamber via pump tubing, wherein the mixing chamber is located above said pneumatic piston and the pump tubing passes through the peristaltic pump head; a spring which is connected to the shaft of the pneumatic piston; and an outlet for dispersing aerosolized material out of the device, wherein the peristaltic pump delivers liquid from the liquid reservoir to the mixture chamber via the pump tubing, said liquid is aerosolized in the mixture chamber during a power stroke of the pneumatic piston.

In another embodiment, the present invention provides a method of using the device disclosed herein to deliver biotechnology treatments and/or therapeutic agents to specific areas of the oral cavity, gingiva or other tissues. In one embodiment, the treatments and/or therapeutic agents are delivered to the interproximal area between and around the teeth.

In one embodiment, the therapeutic agents include, but are not limited to pharmaceutical molecules or chemicals, nucleotides and proteins.

In one embodiment, the therapeutic agents are cytokine solutions. In another embodiment, the cytokine solutions are the Amnion-derived Cellular Cytokine Solution (ACCS) or pooled ACCS.

In one embodiment, the therapeutic agents are delivered with a solution or buffer that is compatible with the therapeutic agents.

BRIEF DESCRIPTION OF THE DRAWINGS

FIG. 1 shows one embodiment of the drug delivery device disclosed herein.

DETAILED DESCRIPTION OF THE INVENTION

The present invention provides a drug delivery device capable of delivering small amounts of therapeutic agents at low pressure to the interproximal area between and around the teeth. For example, the drug delivery device disclosed herein can deliver a small volume (e.g. ~15 µL) of a liquid product aerosolized in air (e.g. ~7000 µL of air) dispersed with minimal force. The device is intended for delivery of a therapeutic agent in an easy and reproducible manner.

The delivery device described herein can deliver a small volume of drug in a controlled and slow manner. In one embodiment, the volume of solution delivered ranges from 1.0 µL to 99 µL. In another embodiment, the volume of solution delivered ranges from 151 µL to 171 µL.

U.S. Pat. No. 8,444,417 describes a method for ameliorating or treating a dental disease, disorder or injury in a patient in need thereof, the method comprising the step of administering to the patient a therapeutically effective amount of Amnion-derived Cellular Cytokine Solution (ACCS) or pooled ACCS, wherein the ACCS or pooled ACCS comprises physiologic levels of VEGF, Angiogenin, PDGF, TGFβ2, TIMP-1 and TIMP-2 that are dissolved in an aqueous solution. In one embodiment, the physiologic levels are ~5-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2. Small amount of such cytokine solution or other therapeutic agents can be aerosolized and delivered by the device disclosed herein.

In one embodiment, the present invention provides a drug delivery device comprising a housing in which a cartridge containing the therapeutic agents to be delivered, a spring and an outlet channel are located. In one embodiment, the spring is capable of providing a pressure of not more than 5 bar when activated. In another embodiment, the outlet channel has a diameter of less than 0.5 mm. In one embodiment, when the spring is activated, the device delivers 10-50 µL of therapeutic agents through the outlet to the subject in need thereof.

In one embodiment, the present invention provides a drug delivery device comprising a small battery-powered electric motor that drives a reduction gear [C] which articulates with a conversion gear [D] (see FIG. 1). The conversion gear simultaneously drives a peristaltic pump head (on the flip side of the conversion gear [D] of FIG. 1) comprising two pump bars and a pneumatic piston [I]. In one embodiment, the electric motor [A] can be powered by a lithium-ion 3.7V (1.85 Wh) battery [B] that is charged by a small induction (wireless) charging pod.

In one embodiment, the peristaltic pump makes one full revolution per active cycle of the electric motor. The axle of the common conversion gear [E] directly drives the peristaltic pump. Platinum-silicon cured pump tubing [F] originates at a liquid reservoir [G], runs through the peristaltic pump head, and terminates at the mixing chamber [H] at the top of the pneumatic piston [I]. There is a small, rubber check valve [J] (check valve #1) which is actuated by flow pressure at the junction of the pump tubing [F] and the mixing chamber [H]. The purpose of check valve #1 is to prevent the backflow of liquid into the pump tubing during the power stroke of the pneumatic piston [I]. Going past check valve #1, the liquid is deposited onto a second, rubber check valve [K] (check valve #2) in the mixing chamber. In one embodiment, the mixing chamber [H] is a cylindrical chamber of ~10 mm in diameter by ~2 mm in height.

In an active cycle of the electric motor, the pneumatic piston [I] is drawn back by the common conversion gear [D]. The larger diameter portion of the conversion gear [D] articulates with the reduction gear [C] driven by the electric motor [A]. The conversion gear [D] makes one full revolution per active cycle. In one embodiment, revolution is controlled by a small metal piece [L] on the conversion gear [D] and a magnetic sensor on the control board [M] to sense when the conversion gear [D] has made one revolution. As part of the conversion gear [D], there is a smaller diameter gear-set close to the axle [N], this gear-set is approximately half a revolution of gears. The half set of gears articulates with a flat, gear-tooth section on the pneumatic piston's plunger shaft [O]. In one embodiment, the draw stroke is performed when the plunger is drawn back against a compression spring [Q] during the middle portion of the active cycle's gear revolution. In one embodiment, the spring used is 2.63 inches in length, 0.50 inches in diameter, and has a spring rate of 1.5 lbs/inch. In one embodiment, the spring is made of stainless steel and consists of 18 coils. In one embodiment, the active stroke [P] of the plunger is ~25 mm creating ~7000 µL of air expressed per power stroke. As the active cycle is concluding the last tooth of the half-gear set, a ~25 mm power stroke is released from the plunger which is powered by the compression spring's reflection. During the draw stroke, check valve #2 [K] is pulled closed and a third check valve [R] (check valve #3) is opened to draw air into the chamber above the piston. During the power stroke, check valve #3 [R] is forced closed and check valve #2 [K] is pushed open to allow air to get into the mixture chamber [H].

The liquid delivered by the peristaltic pump to the top of check valve #2 is aerosolized in the mixture chamber [H] during the power stroke of the pneumatic piston [I]. In one embodiment, ~7000 µL, of air is mixed with the liquid. The aerosolized material then travels through an aperture [T] into a tapering neck and dispersed out of the device through a nozzle. In one embodiment, the aperture [T] is 3 mm in diameter, the tapering neck is 90 mm in length, and the nozzle is 0.5 mm in diameter.

The volume and pressure of the expelled aerosol can be altered by one or more of the following: changing the length and diameter of the pneumatic piston [I], adjusting the length and diameter of pump tubing [F] and the nozzle diameter.

In one embodiment, the volume of solution delivered ranges from 1.0 µL to 99 µL. The volume can be adjusted by changing the inner diameter of the tubing [F] running through the peristaltic pump. One-sized tubing would be selected to deliver a specific volume range of liquid product. In one embodiment, a tubing with inner diameter of 0.0200" can be used to deliver liquids of 12-20 µL. In another embodiment, a tubing with inner diameter of 0.1250" can be used to deliver liquids of 151-171 µL.

The volume of air can be changed by adjusting the length of the power stroke of the piston [I] or the diameter of the piston cylinder. In one embodiment, the piston cylinder is 19 mm in diameter and 76 mm in length. In one embodiment, the piston is drawn back 25 mm during the power stroke. In one embodiment, the volume of air is 7,088 $mm^3$ or 7,088 µL.

The pressure of the air can be adjusted by the changing the spring rate (lbs/inch). In one embodiment, a spring with a rate of 1.5 lbs/inch is used. In another embodiment, a spring with a rate of 4.5 lbs/inch is used, leading to an increase in the air pressure by three times.

The force of the aerosolized liquid leaving the nozzle can be changed by the pressure of the air (i.e. changing the spring rate) and/or the final diameter of the nozzle. The smaller the nozzle diameter the greater the velocity of the aerosolized liquid has when leaving the nozzle and therefore greater force. In one embodiment, the pressure of the air leaving the nozzle is less than 5 bar. In one embodiment, the aperture [T] is 3 mm in diameter, the tapering neck is 90 mm in length, and the nozzle is 0.5 mm in diameter.

The device could be configured to deliver liquids with different viscosities. In one embodiment, the device could be configured to deliver any liquid with a viscosity of 1 centipose (e.g. water). In another embodiment, the device could be configured to deliver any liquid with a viscosity of 2000 centipose (e.g. glycerin). The device can be used to deliver viscous liquids by using more forceful springs, decreasing the nozzle diameter and/or increasing the chamber volume.

The primary advantage of the device is to quickly and repeatedly deliver a specific volume of product to a targeted area. Any liquid product or solid dissolved or suspended in a liquid with an appropriate viscosity can be delivered by the device. In one embodiment, the product comprises pharmaceutical molecules or chemicals including, but not limited to antibiotics, analgesics, astringents, vasodilators. In another embodiment, the product comprises nucleotides including, but not limited to oligonucleotides, siRNA and antisense oligonucleotides. In another embodiment, the product comprises proteins including, but not limited to peptide, proteins, antibodies and monoclonal antibodies. In another embodiment, the device is used to deliver a specific dosage of pharmaceuticals with high value. In one embodiment, the product to be delivered may further comprise a solution or buffer that is compatible with the product.

The present invention also provides a method of using the device disclosed herein to delivery therapeutic agents to specific areas of the oral cavity, gingiva or other tissues.

In one embodiment, the therapeutic agents are delivered to the interproximal area between and around the teeth. The pressure would be regulated in order to ensure the product is delivered to the interproximal area and not blown past the target site.

In summary, the present invention provides a device for delivering therapeutic agents to a subject, the device comprising a peristaltic pump driven by a motor, wherein the peristaltic pump comprises a peristaltic pump head and a pneumatic piston; a liquid reservoir which is connected to a mixing chamber via pump tubing, wherein the mixing chamber is located above said pneumatic piston and the pump tubing passes through the peristaltic pump head; a spring which is connected to the shaft of the pneumatic piston; and an outlet for dispersing aerosolized material out of the device, wherein the peristaltic pump delivers liquid from the liquid reservoir to the mixture chamber via the pump tubing, said liquid is aerosolized in the mixture chamber during a power stroke of the pneumatic piston.

In one embodiment, the peristaltic pump is connected to the motor via a reduction gear and a conversion gear, wherein the reduction gear is articulated with the conversion gear. In another embodiment, the conversion gear comprises a small metal piece that can be detected by a magnetic sensor on a control board to track the revolution of the conversion gear.

In one embodiment, the conversion gear comprises a smaller diameter gear-set close to the axle of the conversion gear, said smaller diameter gear-set articulates with a gear-tooth section on the shaft of the pneumatic piston. In one embodiment, the peristaltic pump makes one full revolution per active cycle of the motor.

In one embodiment, the outlet of the device comprises an aperture, a tapering neck and a nozzle.

In one embodiment, the pneumatic piston is drawn back against the spring and then released, thereby generating a power stroke by the reflection of the compressed spring. In one embodiment, when the pneumatic piston is being drawn back, a valve located in the mixing chamber is closed and a valve located outside the mixing chamber is opened to allow air to enter into a chamber above the pneumatic piston. In another embodiment, when the pneumatic piston is being released, a valve located in the mixing chamber is opened and a valve located outside the mixing chamber is closed to allow air to enter into the mixing chamber.

In one embodiment, the therapeutic agents are selected from the group consisting of pharmaceutical molecules, nucleotides and proteins. For example, the pharmaceutical molecules include, but are not limited to, antibiotics, analgesics, astringents and vasodilators. In another embodiment, the device disclosed herein can deliver nucleotides such as oligonucleotides, siRNA and antisense oligonucleotides etc. In another embodiment, the device disclosed herein can deliver proteins such as peptide, antibodies or monoclonal antibodies. In one embodiment, the present device can deliver cytokine solutions comprising Amnion-derived Cellular Cytokine Solution (ACCS) or pooled ACCS.

The present invention also provides a method of delivering therapeutic agents to a tissue of a subject, comprising the steps of: loading therapeutic agents into the liquid reservoir of the device described herein; aerosolizing the therapeutic agents in the mixing chamber; and delivering the aerosolized therapeutic agents to the tissue. In one embodiment, the tissue is the oral cavity. In one embodiment, the issue is gingiva. In another embodiment, the tissue is the interproximal area between and around the teeth.

In one embodiment, a single shot of 15 microliter of aerosolized therapeutic agent is applied per tooth. In one embodiment, the time taken to deliver the aerosolized therapeutic agent to a tooth is a fraction of second.

It will be understood that the foregoing description is of preferred exemplary embodiments of the invention, and that the invention is not limited to the specific forms shown. These and other modifications may be made in the design and arrangement of the elements described herein without departing from the scope of the invention as expressed in the appended claims.

What is claimed is:

1. A device for delivering therapeutic agents to a subject, comprising
    a) a peristaltic pump driven by a motor, wherein the peristaltic pump comprises a peristaltic pump head and a pneumatic piston;
    b) a liquid reservoir which is connected to a mixing chamber via pump tubing, wherein the mixing chamber is located above said pneumatic piston and the pump tubing passes through the peristaltic pump head;
    c) a spring which is connected to a shaft of the pneumatic piston; and
    d) an outlet channel for dispersing aerosolized therapeutic agents out of the device,
wherein the peristaltic pump delivers liquid from the liquid reservoir to the mixing chamber via the pump tubing, said liquid is aerosolized in the mixing chamber during a power stroke of the pneumatic piston and delivered to the subject, the peristaltic pump is connected to the motor via a reduction gear and a conversion gear, wherein said reduction gear is articulated with said conversion gear and the conversion gear comprises a smaller diameter gear-set close to an axle of the conversion gear, wherein said smaller diameter gear-set articulates with a gear-tooth section on the shaft of the pneumatic piston.

2. A method of using the device of claim 1 to deliver therapeutic agents to a tissue of a subject, comprising the steps of:
    a) loading said therapeutic agents into the liquid reservoir of said device;
    b) aerosolizing said therapeutic agents in the mixing chamber; and
    c) delivering the aerosolized therapeutic agents to the tissue.

3. The method of claim 2, wherein the tissue is an oral cavity.

4. The method of claim 2, wherein the tissue is gingiva.

5. The method of claim 2, wherein the tissue is an interproximal area between and around teeth of an oral cavity.

6. A device for delivering therapeutic agents to a subject, comprising
    a) a peristaltic pump driven by a motor, wherein the peristaltic pump comprises a peristaltic pump head and a pneumatic piston;
    b) a liquid reservoir which is connected to a mixing chamber via pump tubing, wherein the mixing chamber is located above said pneumatic piston and the pump tubing passes through the peristaltic pump head;
    c) a spring which is connected to a shaft of the pneumatic piston; and
    d) an outlet channel for dispersing aerosolized therapeutic agents out of the device,
wherein the peristaltic pump delivers liquid from the liquid reservoir to the mixing chamber via the pump tubing, said liquid is aerosolized in the mixing chamber during a power stroke of the pneumatic piston and delivered to the subject, the pneumatic piston is drawn back against the spring and then released, thereby generating a power stroke by the reflection of the compressed spring, and when the pneumatic piston is being drawn back, a valve located in the mixing chamber is closed and a valve located outside the mixing chamber is opened to allow air to enter into a chamber above the pneumatic piston.

7. A method of using the device of claim 6 to deliver therapeutic agents to a tissue of a subject, comprising the steps of:
    a) loading said therapeutic agents into the liquid reservoir of said device;
    b) aerosolizing said therapeutic agents in the mixing chamber; and
    c) delivering the aerosolized therapeutic agents to the tissue.

8. The method of claim 7, wherein the tissue is an oral cavity.

9. The method of claim 7, wherein the tissue is gingiva.

10. The method of claim 7, wherein the tissue is an interproximal area between and around teeth of an oral cavity.

11. A device for delivering therapeutic agents to a subject, comprising
    a) a peristaltic pump driven by a motor, wherein the peristaltic pump comprises a peristaltic pump head and a pneumatic piston;
    b) a liquid reservoir which is connected to a mixing chamber via pump tubing, wherein the mixing chamber is located above said pneumatic piston and the pump tubing passes through the peristaltic pump head;
    c) a spring which is connected to a shaft of the pneumatic piston; and
    d) an outlet channel for dispersing aerosolized therapeutic agents out of the device,
wherein the peristaltic pump delivers liquid from the liquid reservoir to the mixing chamber via the pump tubing, said liquid is aerosolized in the mixing chamber during a power stroke of the pneumatic piston and delivered to the subject, the pneumatic piston is drawn back against the spring and then released, thereby generating a power stroke by the reflection of the compressed spring, and when the pneumatic piston is being released, a valve located in the mixing chamber is opened and a valve located outside the mixing chamber is closed to allow air to enter into the mixing chamber.

12. A method of using the device of claim 11 to deliver therapeutic agents to a tissue of a subject, comprising the steps of:
    a) loading said therapeutic agents into the liquid reservoir of said device;
    b) aerosolizing said therapeutic agents in the mixing chamber; and
    c) delivering the aerosolized therapeutic agents to the tissue.

13. The method of claim 12, wherein the tissue is an oral cavity.

14. The method of claim 12, wherein the tissue is gingiva.

15. The method of claim 12, wherein the tissue is an interproximal area between and around teeth of an oral cavity.

\* \* \* \* \*